United States Patent [19]

Seino

[11] Patent Number: 4,835,284
[45] Date of Patent: May 30, 1989

[54] METHOD FOR PREPARING 2-PHENYLBENZOTRIAZOLES AND 2-PHENYLBENZOTRIAZOLE-N-OXIDES

[75] Inventor: Shuichi Seino, Kobe, Japan

[73] Assignee: Chemipro Kasei Kaisha, Ltd., Hyogo, Japan

[21] Appl. No.: 149,964

[22] Filed: Jan. 27, 1988

Related U.S. Application Data

[63] Continuation of Ser. No. 899,821, Aug. 25, 1986, abandoned.

[51] Int. Cl.$^4$ .................................. C07D 249/20
[52] U.S. Cl. .................... 548/259; 534/590; 534/845; 534/853; 548/260; 548/261
[58] Field of Search ............ 548/257, 261, 260, 289; 534/590

[56] References Cited

U.S. PATENT DOCUMENTS

4,642,350  2/1987  Davatz ........................ 548/260

FOREIGN PATENT DOCUMENTS

57-167976 10/1982 Japan .................... 548/260
170172   9/1984 Japan .................... 548/260
172481   9/1984 Japan .................... 548/260
8538217  9/1986 Japan .................... 548/260
8538218  9/1986 Japan .................... 548/260

OTHER PUBLICATIONS

Fieser and Fieser, *Organic Chemistry*, 3rd Ed. (1956: Reinhold Publishing Co., N.Y.), pp. 350 and 362.
Ross, K. D. (1975), J. Agric. Food Chem., 23(3), pp. 475–478.
March, J., *Advanced Organic Chemistry*, 2nd ed (1977: McGraw-Hill Book Co., N.Y.), p. 1138.

*Primary Examiner*—Donald G. Daus
*Assistant Examiner*—Mark W. Noel
*Attorney, Agent, or Firm*—Felfe & Lynch

[57] ABSTRACT

This invention relates to a method for preparing 2-phenylbenzotriazoles having the formula I,

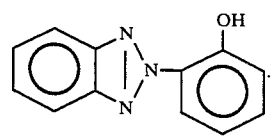

14 Claims, No Drawings

METHOD FOR PREPARING 2-PHENYLBENZOTRIAZOLES AND 2-PHENYLBENZOTRIAZOLE-N-OXIDES

This application is a continuation of application Ser. No. 899,821, filed Aug. 25, 1986, now abandoned.

BACKGROUND OF THE INVENTION (a) Field of the Invention

This invention relates to a method for preparing 2-phenylbenzotriazoles having the following general formula I, which are useful as an ultraviolet ray absorber.

This invention further relates to a method for preparing 2-phenylbenzotriazole-N-oxides having the following general formula II, which are a useful intermediate for said 2-phenylbenzotriazoles.

(b) Description of the Prior Art 2-phenylbenzotriazoles having the following general formula I,

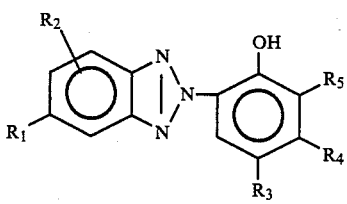

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4) are known to be useful as an ultraviolet ray absorber to be added to plastics, paints, oils and the like.

2-phenylbenzotriazole-N-oxides having the general formula II,

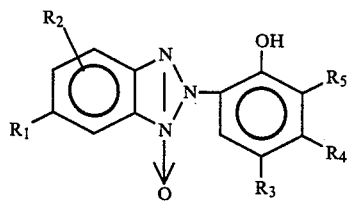

(wherein $R_1$, $R_2$, $R_3$, $R_4$ and $R_5$ are the same as defined above with regard to the general formula I) are known to be a important intermediate for said 2-phenylbenzotriazoles.

Heretofore, these 2-phenylbenzotriazoles and 2-phenylbenzotriazole-N-oxides have been produced by chemically or electrolytically reducing o-nitroazobenzene derivatives having the general formula III,

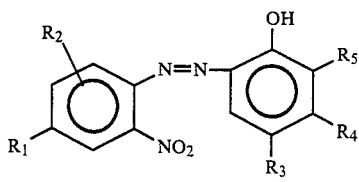

(wherein $R_1$, $R_2$, $R_3$, $R_4$ and $R_5$ are the same as defined above with regard to the general formula I). However, these conventional methods respectively have merits and demerits, and are not always satisfactory.

For example, Japanese Patent Publication No. 37-5934 and U.S. Pat. No. 3,773,751 disclose a method for preparing 2-phenylbenzotriazoles or 2-phenylbenzotriazole-N-oxides by chemically reducing o-nitroazobenzene derivatives in an alcoholic sodium hydroxide solution with zinc powder at a satisfactory yield. However, this sodium hydroxide-zinc system produces zinc sludge which results in waste water contamination problems.

As disclosed in U.S. Pat. No. 2,362,988, ammonium sulfide, alkali-sulfide, zinc-ammonia system, hydrogen sulfide-sodium sulfide system and zinc-hydrochloric acid system are used as a chemical reducing agent for the above mentioned reduction reaction. However, this conventional method produces a large amount of sulfite or zinc salts which result in waste water contamination. The sulfite further generates sulfurous acid gas, and the used sulfide type reducing agent generates poisonous hydrogen sulfide, which results in environmental polution problems.

Japanese Patent Laid Open Nos. 51-138679 and 51-138680 disclose a reduction method by the addition of pressurized hydrogen. Japanese Patent Laid Open No. 50-88072 discloses a reduction method by hydrazine. However, these methods are not satisfactory in view of yield and economy, and it is impossible to obtain the desired product of high purity because of side reaction is caused during the main reaction. Particularly, in the case of producing a chlorine-containing product, a side reaction such as dechlorination reaction is casued.

SUMMARY OF THE INVENTION

An object of the present invention is to provide a novel method for preparing 2-phenylbenzotriazoles and 2-phenylbenzotriazole-N-oxides, which solves the above mentioned problems of the conventional methods.

(i) That is, an object of the present invention is to provide a method for preparing 2-phenylbenzotriazoles having the general formula I,

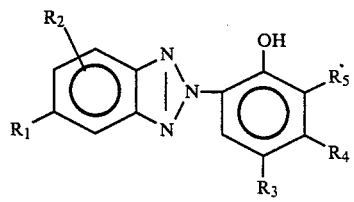

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4), characterized by reducing o-nitroazobenzenes having the general formula III,

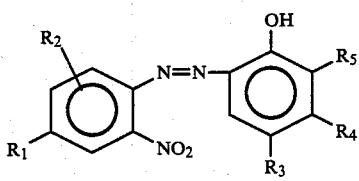

(wherein $R_1$, $R_2$, $R_3$, $R_4$ and $R_5$ are the same as defined above) with saccharides in the presence of a hydrogen transfer catalyst and base.

(ii) Another object of the present invention is to provide a method for preparing 2-phenylbenzotriazoles having the general formula I,

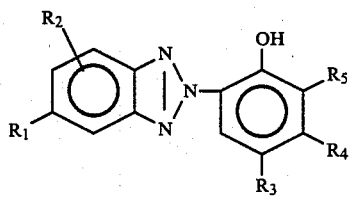

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4), characterized by reducing 2-phenylbenzotriazole-N-oxides having the general formula II,

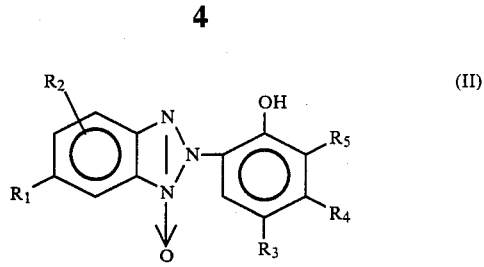

(wherein $R_1$, $R_2$, $R_3$, $R_4$ and $R_5$ are the same as defined above) with saccharides in an amount of 0.5 to 1.5 moles per one mole of said 2-phenylbenzotriazole-N-oxides having the general formula II in the presence of a hydrogen transfer catalyst and base.

(iii) Still other object of the present invention is to provide a method for preparing 2-phenylbenzotriazole-N-oxides having the general formula II,

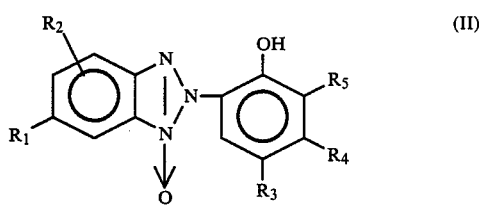

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4), characterized by reducing o-nitroazobenzenes having the general formula III,

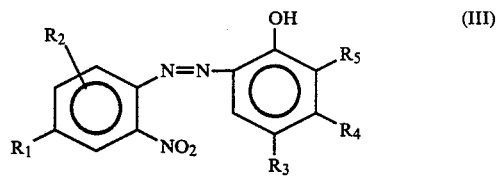

(wherein $R_1$, $R_2$, $R_3$, $R_4$ and $R_5$ are the same as defined above) with saccharides in an amount of 0.5 to 0.8 moles per one mole of o-nitroazobenzenes having the general formula III in the presence of a hydrogen transfer catalyst and base.

DETAILED DESCRIPTION OF THE INVENTION

In order to solve the above mentioned problems of the conventional methods, I have variously studied and found that the desired 2-phenylbenzotriazoles having the general formula I,

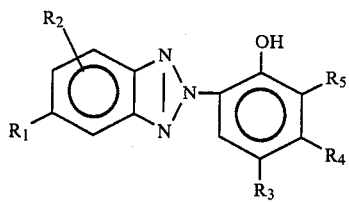

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4) can be produced with technically and economically satisfactory results without causing environmental pollution, by reducing (i) o-nitroazobenzenes having the general formula III,

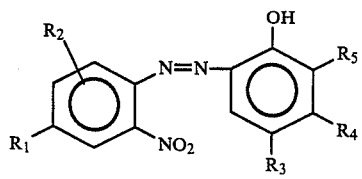

(wherein $R_1$, $R_2$, $R_3$, $R_4$ and $R_5$ are the same as defined above) or (ii) 2-phenylbenzotriazole-N-oxides having the general formula II,

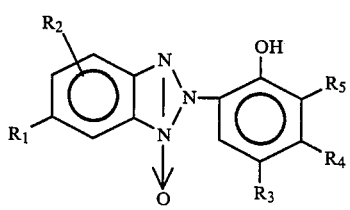

(wherein $R_1$, $R_2$, $R_3$, $R_4$ and $R_5$ are the same as defined above) with saccharides in the presence of a hydrogen transfer catalyst and base.

The method (i) for preparing 2-phenylbenzotriazoles having the general formula I by reducing o-nitroazobenzenes having the general formula II in accordance with the present invention can be carried out by either one step or two steps depending on the conditions of temperature and the amount of saccharides used as mentioned below.

In the case of one step method:

The suitable temperature condition for this process [Process (a)] is about 60° to 80° C., and a saccharide reducing agent is suitably used in an amount of 1 to 2 moles per 1 mole of the starting material, i.e. o-nitroazobenzenes of the general formula III. The reaction is carried out in the following manner.

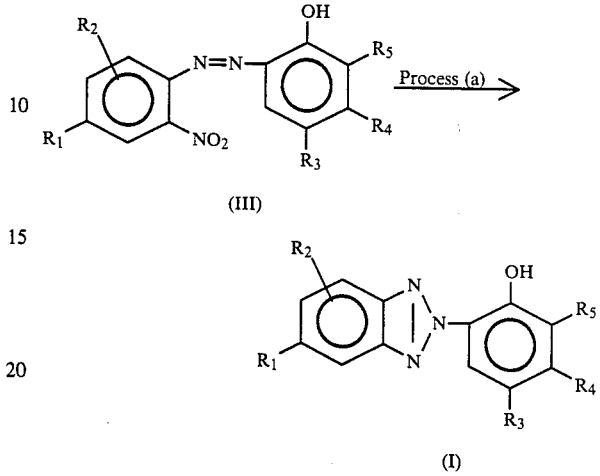

In the case of two step method:

The suitable temperature condition is about 20° to 80° C. at the first step [Process (b)] and about 60° to 100° C. at the second step [Process (c)]. The two step method is sometimes advantageous in view of the quality of product and the yield although it takes two steps. A saccharide reducing agent is suitably used in an amount of 0.5 to 0.8 moles per 1 mole of the starting material, i.e. o-nitroazobenzenes of the general formula III at the first step [Process (b)] and 0.5 to 1.5 moles per 1 mole of the intermediate product, i.e. 2-phenylbenzotriazole-N-oxides of the general formula II at the second step [Process (c)].

The reaction is carried out in the following manner.

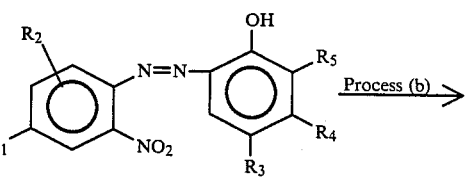

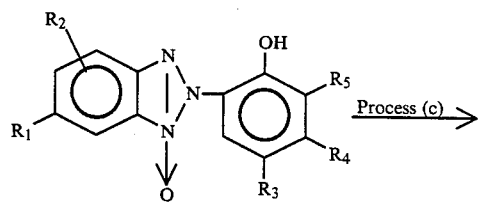

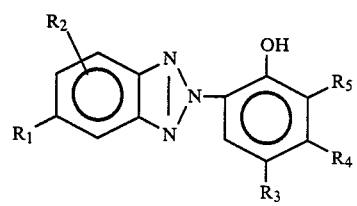

The reaction of the first Process (b) rapidly and exothermally proceeds although it varies depending on the type of the catalyst used.

The method (ii) for preparing 2-phenylbenzotriazoles of the general formula I by reducing 2-phenylbenzotriazole-N-oxides of the general formula II is carried out in the same manner as in the above mentioned Process (c).

In the method (iii), the desired 2-phenylbenzotriazole-N-oxides having the general formula II,

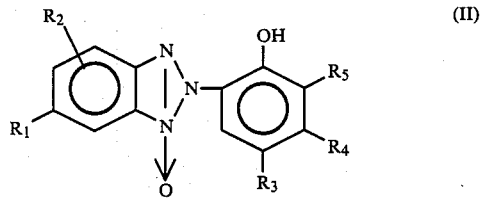

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4) can be produced with technically and economically satisfactory results without causing environmental polution, by reducing o-nitrobenzenes having the general formula III,

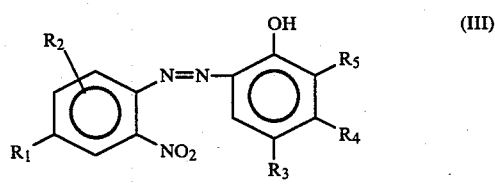

(wherein $R_1$, $R_2$, $R_3$, $R_4$ and $R_5$ are the same as defined above) with saccharides in the presence of a hydrogen transfer catalyst and base.

This reaction is carried out in the following manner.

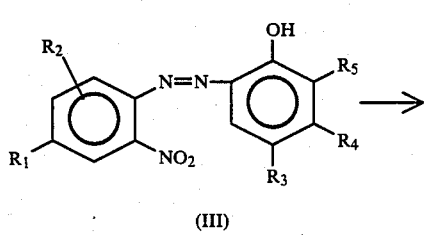

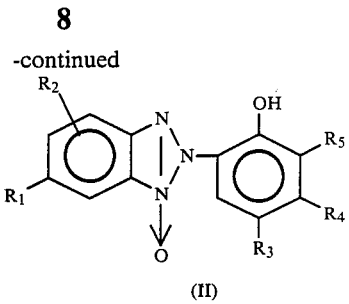

This reaction is the same as that of the above mentioned Process (b), and proceeds rapidly and exothermally at a temperature of 20° to 80° C. although it varies depending on the type of the catalyst used.

In order to smoothly proceed reaction, all the reactions of the above mentioned Process (a), Process (b) and Process (c) are carried out in an aqueous solution, or in an inert solvent such as alcohols, toluene, acetone, dimethylsulfoxide, acetonitrile and the like, or in a mixture of the above mentioned inert solvent with water. If necessary, a surface active agent, a phase-transfer catalyst, and the like may be added.

Examples of o-nitroazobenzenes expressed by the general formula III used as a starting material in the present invention include:

2-nitro-4-chloro-2'-hydroxy-3'-t-butyl-5'-methylazobenzene,
2-nitro-2'-hydroxy-5'-methylazobenzene,
2-nitro-2'-hydroxy-5'-t-octylazobenzene,
2-nitro-2'-hydroxy-5'-t-butylazobenzene,
2-nitro-4-chloro-2'-hydroxy-3',5'-di-t-butylazobenzene,
2-nitro-2'-hydroxy-3',5'-di-t-amylazobenzene,
2-nitro-2'-hydroxy-3',5'-di-t-butylazobenzene,
2-nitro-2'-hydroxy-3'-t-butyl-5'-methylazobenzene,
2-nitro-2',4'-dihydroxyazobenzene,
2-nitro-4-chloro-2',4'-dihydroxyazobenzene,
2-nitro-2'-hydroxy-4'-methoxyazobenzene,
2-nitro-4-chloro-2'-hydroxy-3',5'-di-t-amylazobenzene,
2-nitro-2'-hydroxy-5'-t-amylazobenzene,
2-nitro-4-chloro-2'-hydroxy-5'-t-amylazobenzene,
2-nitro-2'-hydroxy-3',5'-di($\alpha,\alpha$-dimethylbenzyl)azobenzene,
2-nitro-4-chloro-2'-hydroxy-3',5'-di($\alpha,\alpha$-dimethylbenzyl)azobenzene,
2-nitro-2'-hydroxy-3'-$\alpha$-metylbenzyl-5'-methylazobenzene,
2-nitro-4-chloro-2'-hydroxy-3'-$\alpha$-methylbenzyl-5'-methyl azobenzene,
2-nitro-2'-hydroxy-5'-n-dodecylazobenzene,
2-nitro-4-chloro-2'-hydroxy-5'-n-dodecylazobenzene,
2-nitro-2'-hydroxy-3',5'-di-t-octylazobenzene,
2-nitro-4-chloro-2'-hydroxy-3',5'-di-t-octylazobenzene,
2-nitro-4-chloro-2'-hydroxy-5'-t-octylazobenzene,
2-nitro-4-methyl-2'-hydroxy-5'-methylazobenzene,
2-nitro-4-methyl-2'-hydroxy-3'-t-butyl-5-methylazobenzene,
2-nitro-4-n-butyl-2'-hydroxy-3',5'-di-t-butylazobenzene,
2-nitro-4-n-butyl-2'-hydroxy-3'-sec-butyl-5'-t-butylazobenzene,
2-nitro-4-t-butyl-2'-hydroxy-3'-sec-butyl-5'-t-butylazobenzene,
2-nitro-4,6-dichloro-2'-hydroxy-5'-t-butylazobenzene,
2-nitro-4,6-dichloro-2'-hydroxy-3',5'-di-t-butylazobenzene, and
2-nitro-4-carboxy-2'-hydroxy-5-methylazobenzene.

2-phenylbenzotriazole-N-oxides of the general formula II are prepared by reducing o-nitroazobenzenes of the general formula III in accordance with the above mentioned Process (b), examples of which include:

2-(2-hydroxy-3-t-butyl-5-methylphenyl)-5-chlorobenzotriazole-N-oxide, 2-(2-hydroxy-3,5-di-t-butylphenyl)-5-chlorobenzotriazole-N-oxide, 2-(2-hydroxy-3,5-di-t-amylphenyl)benzotriazole-N-oxide, 2-(2-hydroxy-5-methylphenyl)benzotriazole-N-oxide, 2-(2-hydroxy-5-t-butylphenyl)benzotriazole-N-oxide, 2-(2-hydroxy-5-t-octylphenyl)benzotriazole-N-oxide, 2-(2-hydroxy-3,5-di-t-butylphenyl)benzotriazole-N-oxide, 2-(2-hydroxy-3-t-butyl-5-methylphenyl)benzotriazole-N-oxide, 2-(2,4-dihydroxyphenyl)benzotrizole-N-oxide, 2-(2,4-dihydroxyphenyl)-5-chlorobenzotriazole-N-oxide, 2-(2-hydroxy-4-methoxyphenyl)benzotriazole-N-oxide, 2-[2-hydroxy-3,5-di($\alpha,\alpha$-dimethylbenzyl)phenyl]benzotrizole-N-oxide, and 2-(2-hydroxy-3-$\alpha$-methylbenzyl-5-methylphenyl)benzotrizole-N-oxide.

It is preferable to prepare these 2-phenyltriazole-N-oxides of the general formula II by reducing o-nitroazobenzenes of the general formula III as a starting material in accordance with the above mentioned Process (b), but these materials can also be prepared by other known methods.

Examples of a saccharide reducing agent, i.e. hydrogen atom donor include glucose, fructose, lactose, maltose and the like. Among them, glucose is most preferable.

These saccharide reducing agents are used in an amount of 1 to 2 moles per one mole of o-nitroazobenzenes of the general formula III when 2-phenylbenzotriazoles of the general formula I are prepared from said o-nitroazobenzenes by one step as shown in the above mentioned Process (a) [Method (i)].

These saccharide reducing agents are used in an amount of 0.5 to 1.5 moles per one mole of 2-phenylbenzotriazole-N-oxides of the general formula II when 2-phenylbenzotriazoles of the general formula I are prepared from said 2-phenylbenzotriazole-N-oxides as shown in the above mentioned Process (c) [Method (ii)].

These saccharide reducing agents are used in an amount of 0.5 to 0.8 moles per one mole of o-nitroazobenzenes of the general formula III when 2-phenylbenzotriazole-N-oxides of the general formula II are prepared from said o-nitroazobenzenes as shown in the above mentioned Process (b) [Method (iii)].

A hydrogen transfer catalyst is a material which catalytically acts by receiving hydrogen from a reducing agent and giving hydrogen to a material to be reduced, or by giving hydrogen to a material to be reduced and then taking hydrogen from a reducing agent.

Examples of the hydrogen transfer catalyst include 2,3-dichloro-1,4-naphthoquinone; 1,4-naphthoquinone; 1,2-naphthoquinone; 2,6-naphthoquinone; naphthoquinone having an alkyl group or an alkoxyl group in the nucleus; 1,4-benzoquinone; 2-chloro-1,4-benzoquinone; 2,3-dichloro-5,6-dicyanobenzoquinone; chloroanil; tetrachloro-1,2-benzoquinone; 4,4'-diphenoquinone; 3,3',5,5'-tetrachloro-4,4'-diphenoquinone; phenanthrenequinone; anthraquinone; anthraquinone substituted with alkyl group, alkoxyl group, halogen atom, amino group, carboxyl group, or sulfonic acid group; benzophenone; benzophenone substituted with alkyl group, alkoxyl group, halogen atom, or hydroxyl group; benzanthrone; anthrone; 9-fluorenone; 9-xanthenone; and various hydroquinones respectively corresponding to the above mentioned quinones (for example, 2,3-dichloro-1,4-dioxynaphthalene corresponding to 2,3-dichloro-1,4-naphthoquinone). Among them, preferable examples include 2,3-dichloro-1,4-naphthoquinone; benzoquinone; anthraquinone; 9-fluorenone; benzanthrone; hydroquinone; 1,4-dihydroxynaphthalene and the like.

These hydrogen transfer catalysts may be used alone or in a mixture of two or more.

In the above mentioned Processes (a), (b) and (c), a hydrogen transfer catalyst is used generally in an amount of 0.2 to 30%, preferably 2 to 20% on the basis of the weight of the starting material, i.e. o-nitroazobenzenes or 2-phenylbenzotriazole-N-oxides.

Examples of the base used in the present invention include sodium hydroxide, potassium hydroxide and the like. The base is used in an amount of 1 to 12 moles, preferably 2 to 8 moles per one mole of the starting material, i.e. o-nitroazobenzenes or 2-phenylbenzotriazole-N-oxides.

The present invention is further illustrated by the following Examples.

EXAMPLE 1

2-nitro-2'-hydroxy-3',5'-di-t-amylazobenzene 12.8 g was added to a mixture of methanol 41 g, water 10 g and 97% sodium hydroxide 11 g, and the resultant mixture was stirred at 65° C. for 30 minutes. Thereafter, 9-fluorenone 2.0 g and then glucose 12 g were added to the mixture at 60° to 65° C. over 4 hours. The resultant mixture was further stirred for 4 hours at the boiling point (70° C.), thus completing the reduction reaction.

Thereafter, water 50 ml was added to the reaction liquor, and the reaction liquor was neutralized with 62% sulfuric acid 13 g. The liquor thus neutralized was cooled to 20° C. to precipitate a crystal. The crystal thus obtained was separated by filtration, and the separated crystal was fully washed with water and further with methanol. The washed crystal was then dried, thus producing 9.9 g of 2-(2'-hydroxy-3',5'-di-t-amylphenyl)-benzotriazole having a melting point of 77° to 79° C. at the yield of 85.0%.

EXAMPLE 2

97% sodium hydroxide 9.6 g was added to methanol 100 ml, and was stirred at 65° C. for 30 minutes. After cooling to 50° C., 2-nitro-4-chloro-2'-hydroxy-3'-t-butyl-5'-methylazobenzene 11.6 g was added to the resultant mixture over 30 minutes, and thereafter 2,3-dichloro-1,4-naphthoquinone 0.7 g was added. Glucose 8 g was added to the resultant mixture at 40° to 45° C. over one hour, and the mixture was stirred for one hour at 40° to 45° C. As this result, almost all of the azobenzenes disappeared to produce 2-(2'-hydroxy-3'-t-butyl-5'-methylphenyl)-5-chlorobenzotriazole-N-oxide, thus the reaction of Process (b) being completed.

In order to conduct the reaction of Process (c), the system was heated, and was stirred at 64° to 67° C. for two hours. As this result, the N-oxide disappeared, thus Process (c) being completed. Thereafter, water 50 ml was added to the reaction liquor, and the resultant reaction liquor was neutralized with 62% sulfuric acid 11 g to precipitate a crystal. The precipitated crystal was separated by filtration, and the separated crystal was fully washed with hot water of 60° to 70° C. and further with a small amount of methanol. The washed crystal was then dried, thus obtaining 9.4 g of 2-(2'-hydroxy-3'-t-butyl-5'-methylphenyl)-5-chlorobenzotriazole having a melting point of 138° to 140° C. at the yield of 89.5%.

EXAMPLE 3

The same procedure as in Example 2 was repeated, except that 2-nitro-4-chloro-2'-hydroxy-3'-t-butyl-5'-methylazobenzene 11.6 g was replaced respectively by (a) 2-nitro-4-chloro-2'-hydroxy-3',5'-di-t-butylazobenzene 13.0 g and (b) 2-nitro-2'-hydroxy-3',5'-di-t-amylazobenzene 12.8 g.

The products thus obtained and their properties are as follow:

(a) 2-(2'-hydroxy-3',5'-di-t-butylphenyl)-5-chlorobenzotriazole:
Yield: 10.5 g (88.0%), Melting Point: 154° to 155.5° C.
(b) 2-(2'-hydroxy-3',5'-di-t-amylphenyl)benzotriazole:
Yield: 10.1 g (86.0%), Melting Point: 77° to 79° C.

EXAMPLE 4

97% sodium hydroxide 8.2 g was added and dissolved in a mixture of methanol 60 ml and water 20 ml. 2-nitro-4-chloro-2'-hydroxy-3'-t-butyl-5'-methylazobenzene 11.6 g was then added to the resultant solution at 50° to 60° C. over 30 minutes while stirring, and thereafter 2,3-dichloro-1,4-naphthoquinone 0.3 g and 9-fluorenone 0.4 g were added to the solution. Glucose 8 g was then added to the resultant mixture at 40° to 50° C. over two hours, and the mixture was stirred for one hour at the same temperature. As this result, almost all of the azobenzene disappeared to produce 2-(2-hydroxy-3-t-butyl-5-methylphenyl)-5-chlorobenzotriazole-N-oxide, thus Process (b) being completed.

In order to conduct the reaction of Process (c), the system was heated, and was stirred at 66° to 68° C. (boiling point) for 5 hours. As this result, the N-oxide disappeared, thus Process (c) being completed. Thereafter, water 50 ml was added to the reaction liquor, and the resultant reaction liquor was neutralized with 62% sulfuric acid 10 g to precipitate a crystal. The precipitated crystal was separated by filtration, and the separated crystal was fully washed with hot water of 60° to 70° C. and further with a small amount of methanol. The washed crystal was then dried, thus obtaining 8.7 g of 2-(2'-hydroxy-3'-t-butyl-5'-methylphenyl)-5-chlorobenzotriazole having a melting point of 138° to 140° C. at the yield of 82.9%.

EXAMPLE 5

Water 70 ml, 97% sodium hydroxide 5.2 g, 2-nitro-2'-hydroxy-5'-methylazobenzene 12.9 g and toluene 10 ml were mixed and heated to 60° C. After stirring, hydroquinone 0.6 g was added and glucose 5.0 g was added to the mixture over one hour at 40° to 45° C. The mixture was further stirred for two hours, and the azobenzene disappeared, thus Process (b) being completed. The reaction liquor was neutralized with 62% sulfuric acid 5.8 g, and was cooled to 20° C. to precipitate a crystal. The crystal thus precipitated was separated by filtration to obtain a wet product 12 g of 2-(2'-hydroxy-5'-methylphenyl)benzotriazole-N-oxide (dry weight: 10.8 g, yield 90.0%, and melting point: 138° to 140° C.).

To the wet product 12 g thus obtained, were added methanol 60 ml, water 30 ml, 97% sodium hydroxide 13.0 g and 9-fluorene 0.5 g, and glucose 5.5 g was further added to the mixture over one hour while stirring at 50° to 55° C. The mixture was reacted while stirring at 75° C. (boiling point) for 5 hours. As this result, the N-oxide disappeared, thus Process (c) being completed. The reaction liquor was neutralized with 62% sulfuric acid 19.8 g to pH 8 to precipitate a crystal. The precipitated crystal was separated by filtration, and the separated crystal was fully washed with water and further with methanol. The washed crystal was then dried, thus obtaining 9.4 g of 2-(2'-hydroxy-5'-methylphenyl)benzotriazole having a melting point of 128° to 130° C. at the yield of 92.8%.

EXAMPLE 6

The same procedure as in Example 5 was repeated, except that 9-fluorenone 0.5 g was replaced respectively by (a) benzanthrone 1.0 g, (b) benzophenone 1.5 g and (c) anthrone 1.0 g to produce 2-(2'-hydroxy-5'-methylphenyl)benzotriazole.

The products were obtained with the following yields.

(a) Yield: 9.0 g (88.8%), Melting Point: 128°~130° C.;
(b) Yield: 8.0 g (78.9%), Melting Point: 127.7°~130° C.; and (c) Yield: 8.2 g (80.9%), Melting Point: 128°~130° C.

EXAMPLE 7

97% sodium hydroxide 14.4 g was added to a mixture of methanol 72 ml and water 36 ml. 2-nitro-2'-hydroxy-5'-t-butylazobenzene 15.0 g was then added to the resultant mixture and the mixture was heated to 45°~50° C. Hydroquinone 0.4 g and then glucose 5.0 g were added to the heated mixture over 30 minutes while stirring. The mixture was further stirred for one hour. As this result, the azobenzene disappeared to produce 2-(2'-hydroxy-5'-t-butylphenyl)benzotriazole-N-oxide, thus the reaction of Process (b) being completed.

9-fluorenone 0.7 g was then added to the reaction liquor thus obtained, and the liquor was heated to 55°~60° C. Thereafter, glucose 6.0 g was added to the reaction liquor over 30 minutes, and the reaction was conducted at 75° C. (boiling point) for 6 hours. As this result, the N-oxide disappeared, thus Process (c) being completed. Thereafter, pH of the reaction liquor was made to 8 with 62% sulfuric acid 19.0 g to precipitate a crystal. The precipitated crystal was separated by filtration, and the separated crystal was fully washed with water and further with methanol. The washed crystal was then dried, thus obtaining 11.6 g of 2-(2'-hydroxy-5'-t-butylphenyl)benzotriazole.

EXAMPLE 8

The same procedure as in Example 7 was repeated, except that 2-nitro-2'-hydroxy-5'-t-butylazobenzene 15.0 g was replaced by 2-nitro-2'-hydroxy-5'-t-octylazobenzene 17.7 g, thus producing 13.7 g of 2-(2'-hydroxy-5'-t-octylphenyl)benzotriazole having a melting point of 103° to 105° C. at the yield of 85.0%.

EXAMPLE 9

A mixture of methanol 60 ml, water 30 ml, 97% sodium hydroxide, 12.4 g and 2-nitro-2'-hydroxy-5'-methyl azobenzene 12.9 g was heated and stirred at 45°~50° C. 9-fluorenone 1.0 g and then glucose 5.5 g were added to the resultant mixture over 30 minutes while stirring. The mixture was further stirred at 75° C. (boiling point) for 7 hours. As this result, the azobenzene disappeared to produce 2-(2'-hydroxy-5'-methylphenyl)benzotriazole-N-oxide, thus the reaction of Process (b) being completed.

Glucose 6 g was then added to the reaction liquor over 30 minutes and the reaction was conducted at 75° C. (boiling point) for further 6 hours. As this result, the above prepared N-oxide disappeared, thus the reaction of Process (c) being completed.

Thereafter, water 50 ml was added to the reaction liquor, and the resultant reaction liquor was neutralized with 62% sulfuric acid 15 g to precipitate a crystal. The precipitated crystal was separated by filtration, and the separated crystal was fully washed with water and further with methanol. The washed crystal was then dried, thus obtaining 9.6 g of 2-(2'-hydroxy-5'-methylphenyl)benzotriazole having a melting point of 128° to 130° C. at the yield of 85.0%.

EXAMPLE 10

97% sodium hydroxide 8.2 g was added to methanol 100 ml, and the mixture was stirred at 65° C. for 30 minutes. After cooling to 50° C., 2-nitro-4-chloro-2'-hydroxy-3'-t-butyl-5'-methylazobenzene 11.6 g was added to the resultant mixture over 30 minutes, and thereafter 2,3-dichloro-1,4-naphthoquinone 0.7 g was added. Glucose 4 g was then added to the resultant mixture at 40° to 45° C. over one hour, and the mixture was further stirred for one hour at 40° to 45° C. As this result, almost all of the azobenzene disappeared to produce 2-(2'-hydroxy-3'-t-butyl-5'-methylphenyl)-5-chlorobenzotriazole-N-oxide.

After the reaction, water 50 ml was added to the reaction liquor, and the resultant reaction liquor was neutralized with 62% sulfuric acid 10 g to precipitate a crystal. The precipitated crystal was separated by filtration, and the separated crystal was fully washed with hot water of 60° to 70° C. and further with a small amount of methanol. The washed crystal was then dried, thus obtaining 10.6 g of 2-(2'-hydroxy-3'-t-butyl-5'-methylphenyl)-5-chlorobenzotriazole-N-oxide having a melting point of 161° to 163° C. at the yield of 96.0%.

EXAMPLE 11

The same procedure as in Example 10 was repeated, except that 2-nitro-4-chloro-2'-hydroxy-3'-t-butyl-5'-methylazobenzene 11.6 g was replaced respectively by (a) 2-nitro-4-chloro-2'-hydroxy-3',5'-di-t-butylazobenzene 13.0 g and (b) 2-nitro-2'-hydroxy-3',5'-di-t-amylazobenzene 12.8 g.

The products thus obtained and their properties are as follow:
(a) 2-(2'-hydroxy-3',5'-di-t-butylphenyl)-5-chlorobenzotriazole-N-oxide:
Yield: 11.8 g (95.0%), Melting Point: 178° to 180° C.
(b) 2-(2'-hydroxy-3',5'-di-t-amyphenyl)benzotriazole-N-oxide:
Yield: 11.4 g (93.5%), Melting Point: 110° to 113° C.

EXAMPLE 12

97% sodium hydroxide 8.2 g was added and dissolved in a mixture of methanol 60 ml and water 20 ml. 2-nitro-4-chloro-2'-hydroxy-3'-t-butyl-5'-methylazobenzene 11.6 g was then added to the resultant solution at 50° to 60° C. over 30 minutes while stirring, and thereafter 2,3-dichloro-1,4-naphthoquinone 0.3 g and 9-fluorenone 0.4 g were added to the solution. Glucose 4 g was then added to the resultant mixture at 40° to 50° C. over two hours, and the mixture was stirred for one hour at the same temperature. As this result, almost all of the azobenzene disappeared to produce 2-(2'-hydroxy-3'-t-butyl-5'-methylphenyl)-5-chlorobenzotriazole-N-oxide.

After the reaction, water 50 ml was added to the reaction liquor, and the resultant reaction liquor was neutralized with 62% sulfuric acid 10 g to precipitate a crystal. The precipitated crystal was separated by filtration, and the separated crystal was fully washed with hot water of 60° to 70° C. and further with a small amount of methanol. The washed crystal was then dried, thus obtaining 10.7 g of 2-(2'-hydroxy-3'-t-butyl-5'-methylphenyl)-5-chlorobenzotriazole-N-oxide having a melting point of 162° to 163° C. at the yield of 96.8%.

EXAMPLE 13

Water 70 ml, 97% sodium hydroxide, 5.2 g, 2-nitro-2'-hydroxy-5'-methylazobenzene 12.9 g and toluene 10 ml were mixed and heated to 60° C. After stirring, hydroquinone 0.6 g was added and glucose 5.0 g was added to the mixture over one hour at 40° to 45° C. The mixture was further stirred for two hours, and the azobenzene disappeared, thus the reaction of Process (b) being completed. The reaction liquor was neutralized with 62% sulfuric acid 5.8 g, and was cooled to 20° C. to precipitate a crystal. The crystal thus precipitated was separated by filtration and was dried, thus producing 10.8 g of 2-(2'-hydroxy-5'-methylphenyl)benzotriazole-N-oxide having a melting point of 138° to 140° C. at the yield of 90.0%.

EXAMPLE 14

97% sodium hydroxide 14.4 g was added to a mixture of methanol 72 ml and water 36 ml, 2-nitro-2'-hydroxy-5'-t-butylazobenzene 15.0 g was then added to the resultant mixture and the mixture was heated to 45°∼50° C. Hydroquinone 0.4 g and then glucose 5.0 g were added to the heated mixture over 30 minutes while stirring. The mixture was further stirred for one hour. As this result, the azobenzene disappeared to produce 2-(2'-hydroxy-5'-t-butylphenyl)benzotriazole-N-oxide.

Water 50 ml was added to the reaction liquor thus obtained, and the liquor was neutralized with 62% sulfuric acid 23 g to precipitate a crystal. The precipitated crystal was separated by filtration, and the separated crystal was fully washed with water and further with methanol. The washed crystal was then dried, thus obtaining 12.9 g of 2-(2'-hydroxy-5'-t-butylphenyl)benzotriazole-N-oxide having a melting point of 73° to 78° C. at the yield of 91.1%.

EXAMPLE 15

The same procedure as in Example 14 was repeated, except that 2-nitro-2'-hydroxy-5'-t-butylazobenzene 15.0 g was replaced by 2-nitro-2'-hydroxy-5'-t-octylazobenzene 17.7 g, thus producing 15.2 g of 2-(2'-hydroxy-5'-t-octylphenyl)benzotriazole-N-oxide having a melting point of 106.0° to 111.0° C. at the yield of 90.2%.

EXAMPLE 16

A mixture of methanol 60 ml, water 30 ml, 97% sodium hydroxide 12.4 g and 2-nitro-2'-hydroxy-5'-methylazobenzene 12.9 g was heated and stirred at 45°∼50° C. 9-fluorenone 1.0 g and then glucose 5.5 g were added to the resultant mixture over 30 minutes while stirring. The mixture was further stirred at 75° C.

(boiling point) for 7 hours. As this result, the azobenzene disappeared to produce 2-(2'-hydroxy-5'-methylphenyl)benzotriazole-N-oxide.

Water 50 ml was added to the reaction liquor thus obtained, and the liquor was neutralized with 62% sulfuric acid 19 g to precipitate a crystal. The crystal thus obtained was separated by filtration, and the separated crystal was fully washed with water and further with methanol. The crystal thus washed was dried to produce 11.1 g of 2-(2'-hydroxy-5'-methylphenyl)benzotriazole having a melting point of 138° to 140° C. at the yield of 92.1%.

What we claim is:

1. A method for preparing a 2-phenylbenzotriazole having formula

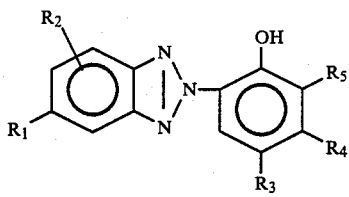

wherein $R_1$ represents hydrogen or chlorine a lower alkyl group having a carbon number of 1 to 4, a lower alkoxy group having a carbon number of 1 to 4, a carboxyl group or a sulfonic acid group; $R_2$ represents hydrogen or chlorine, a lower alkyl group having a carbon number of 1 to 4 or a lower alkoxy group having a carbon number of 1 to 4; $R_3$ represents a hydrogen or chlorine, an alkyl group having a carbon number of 1 to 12, a lower alkoxy group having a carbon number of 1 to 4, a phenyl group, a phenyl group substituted with an alkyl group having a carbon number of 1 to 8, a phenyl group or a phenylalkyl group, the alkyl part of which has a carbon number of 1 to 4; $R_4$ represents hydrogen or chlorine, a hydroxyl group or a lower alkoxyl group having a carbon number of 1 to 4; and $R_5$ represents hydrogen, an alkyl group having a carbon number of 1 to 12 or a phenyl alkyl group, the alkyl part of which has a carbon number of 1 to 4 comprising reducing a o-nitroazobenzene having the formula:

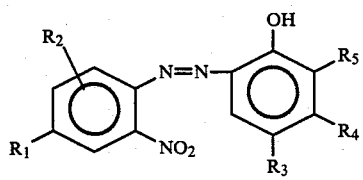

with a reducing saccharide selected from the group consisting of glucose, fructose, lactose and maltose in the presence of a hydrogen transfer catalyst selected from the group consisting of 9-fluorenone, benzanthrone, hydroquinone and 1,4-dihydroxynapthalene and a base in an aqueous medium.

2. The method as claimed in claim 1, wherein said method is carried out by one step in the presence of said reducing saccharide, in an amount of 1 to 2 moles per one mole of said o-nitroazobenzene.

3. The method as claimed in claim 1, wherein said method is carried out in two steps, the first step taking place in the presence of said reducing saccharide in an amount of 0.5 to 0.8 moles per one mole of said o-nitrobenzene to produce an intermediate product of 2-phenylbenzotriazole-N-oxide and the second step taking place in the presence of said reducing saccharide in an amount of 0.5 to 1.5 moles per one mole of said intermediate product to produce said 2-phenylbenzotriazole. .

4. The method as in claim 1, wherein said hydrogen transfer catalyst is used in an amount of 0.2 to 30% on the basis of the weight of said o-nitroazobenzene.

5. The method as in claim 1, wherein said base is sodium hydroxide or potassium hydroxide, and is used in an amount of 1 to 12 moles per one mole of said o-nitroazobenzene.

6. The method of claim 1, wherein said reducing saccharide is glucose.

7. A method for preparing a 2-phenylbenzotriazole having the formula

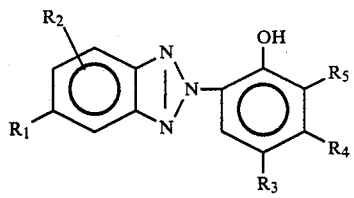

wherein $R_1$ represents hydrogen or chlorine, a lower alkyl group having a carbon number of 1 to 4, a lower alkoxyl group having a carbon number of 1 to 4, a carboxyl group or a sulfonic acid group; $R_2$ represents hydrogen or chlorine, a lower alkyl group having a carbon number of 1 to 4 or a lower alkoxyl group having a carbon number of 1 to 4, $R_3$ represents hydrogen or chlorine, an alkyl group having a carbon number of 1 to 12, a lower alkoxyl group having a carbon number of 1 to 4, a phenyl group, a phenyl group substituted with an alkyl group having a carbon number of 1 to 8, a phenoxy group or a phenylalkyl group, the alkyl part of which has a carbon number of 1 to 4; $R_4$ represents hydrogen or chlorine, a hydroxyl group or a lower alkyl group having a carbon number of 1 to 4; and $R_5$ represents hydrogen, an alkyl group having a carbon number of 1 to 12 or a phenylalkyl group, the alkyl part of which has a carbon number of 1 to 4, comprising reducing a 2-phenylbenzotriazole-N-oxide having the formula

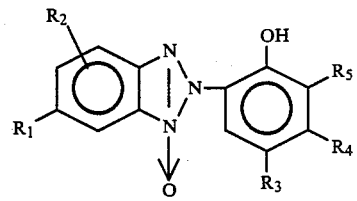

with a reducing saccharide selected from the group consisting of glucose, fructose, lactose and maltose in an amount of 0.5 to 1.5 moles per one mole of said 2-phenylbenzotriazole-N-oxide in the presence of a hydrogen transfer catalyst selected from the group consisting of 9-fluorenone, benzanthrone, hydroquinone and 1,4-dihydroxynaphthalene and a base in an aqueous medium.

8. The method as in claim 7, wherein said hydrogen transfer catalyst is used in an amount of 0.2 to 30% on the basis of the weight of said 2-phenylbenzotriazole-N-oxide.

9. The method as in claim 7, wherein said base is sodium hydroxide or potassium hydroxide, and is used in an amount of 1 to 12 moles per one mole of said 2-phenylbenzotriazole-N-oxide.

10. The method of claim 7, wherein said reducing saccharide is glucose.

11. A method for preparing a 1-phenylbenzotriazole-N-oxide having the formula:

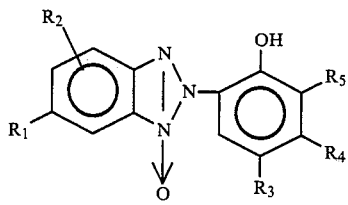

wherein $R_1$ represents hydrogen or chlorine, a lower alkyl group having a carbon number of 1 to 4, a lower alkoxyl group having a carbon number of 1 to 4, a carboxyl group or a sulfonic acid group; $R_2$ represents hydrogen or chlorine, a lower alkyl group having a carbon number of 1 to 4 or a lower alkoxyl group having a carbon number of 1 to 4; $R_3$ represents hydrogen or chlorine, an alkyl group having a carbon number of 1 to 4, a phenyl group, a phenyl group substituted with an alkyl group having a carbon number of 1 to 8, a phenoxy group or a phenylalkyl group, the alkyl part of which has a carbon number of 1 to 4; $R_4$ represents hydrogen or chlorine, a hydroxyl group or a lower alkoxyl group having a carbon number of 1 to 4; and $R_5$ represents hydrogen, an alkyl group having a carbon number of 1 to 12 or a phenylalkyl group, the alkyl part of which has a carbon number of 1 to 4 comprising reducing an o-nitroazobenzene having the formula:

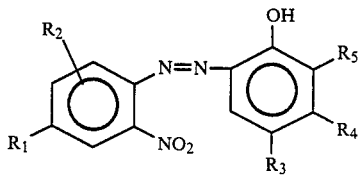

with a reducing saccharide selected from the group consisting of glucose, fructose, lactose and maltose in an amount of 0.5 to 0.8 moles per one mole of said o-nitroazobenzene in the presence of a hydrogen transfer catalyst selected from the group consisting of 9-fluorenone, benzanthrone, hydroquinone, and 1,4-dihydroxynaphthalene and a base in an aqueous medium.

12. The method as in claim 11, wherein said hydrogen transfer catalyst is used in an amount of 0.2 to 30% on the basis of the weight of said o-nitroazobenzene.

13. The method as in claim 11, wherein said base is sodium hydroxide or potassium hydroxide, and is used in an amount of 1 to 12 moles per one mole of said o-nitroazobenzene.

14. The method of claim 11, wherein said reducing saccharide is glucose.

* * * * *